United States Patent [19]

Krag

[11] 4,315,517
[45] Feb. 16, 1982

[54] DEVICE FOR CLEANING TEETH TO PREVENT THE FORMATION OF PLAQUE

[76] Inventor: Mark D. Krag, 217 Edelen Ave., Los Gatos, Calif. 95030

[21] Appl. No.: 956,249

[22] Filed: Oct. 31, 1978

[51] Int. Cl.³ .............................................. A61C 15/00
[52] U.S. Cl. ...................................................... 132/89
[58] Field of Search ..................... 132/89, 91, 92, 93; 206/63.3; 215/228, 355; 401/132, 261, 34; 32/1; 128/272; 15/104.94

[56] References Cited

U.S. PATENT DOCUMENTS

| | | | |
|---|---|---|---|
| 1,287,926 | 12/1918 | Ecaubert | 132/92 A |
| 1,637,153 | 7/1927 | Lawton | 401/34 |
| 2,162,240 | 6/1939 | Boldusoff | 132/91 |
| 2,180,522 | 11/1939 | Henne | 132/91 |
| 2,443,415 | 6/1948 | Buscarino | 132/91 |
| 2,804,203 | 8/1957 | Harkness et al. | 206/63.3 |
| 3,472,247 | 10/1969 | Borsum et al. | 132/91 |
| 3,789,858 | 2/1974 | Pesce | 132/89 |
| 3,903,601 | 9/1975 | Anderson | 32/14 D |
| 4,011,658 | 3/1977 | Tarrson | 132/93 |
| 4,016,892 | 4/1977 | Chodorow | 132/91 |
| 4,142,538 | 3/1979 | Thurnton | 132/89 |
| 4,155,216 | 5/1979 | Griset, Jr. | 132/89 |
| 4,162,687 | 7/1979 | Lorch | 132/91 |

Primary Examiner—G. E. McNeill
Attorney, Agent, or Firm—John J. Leavitt

[57] ABSTRACT

Presented is a device utilizing a thread-like member for "flossing" teeth to dislodge and remove adherent material that may develop into plaque.

9 Claims, 15 Drawing Figures

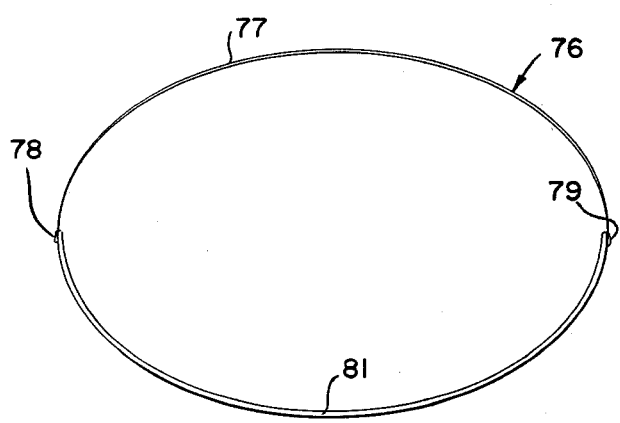
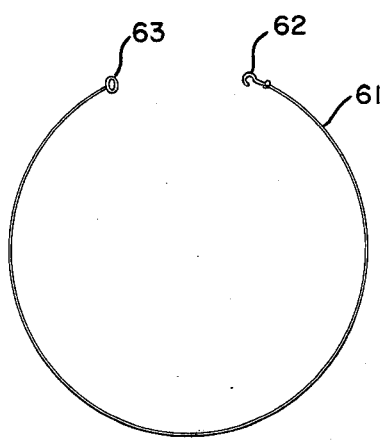
FIG. 14      FIG. 12
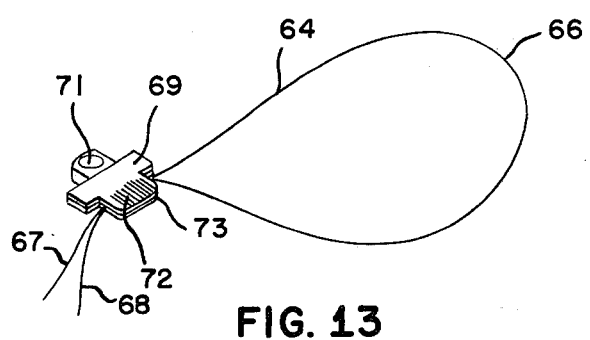
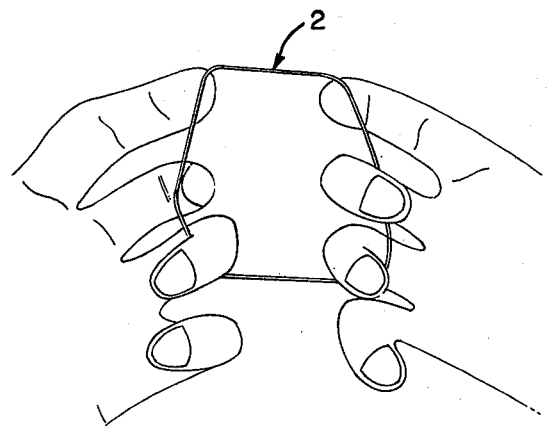
FIG. 13      FIG. 15
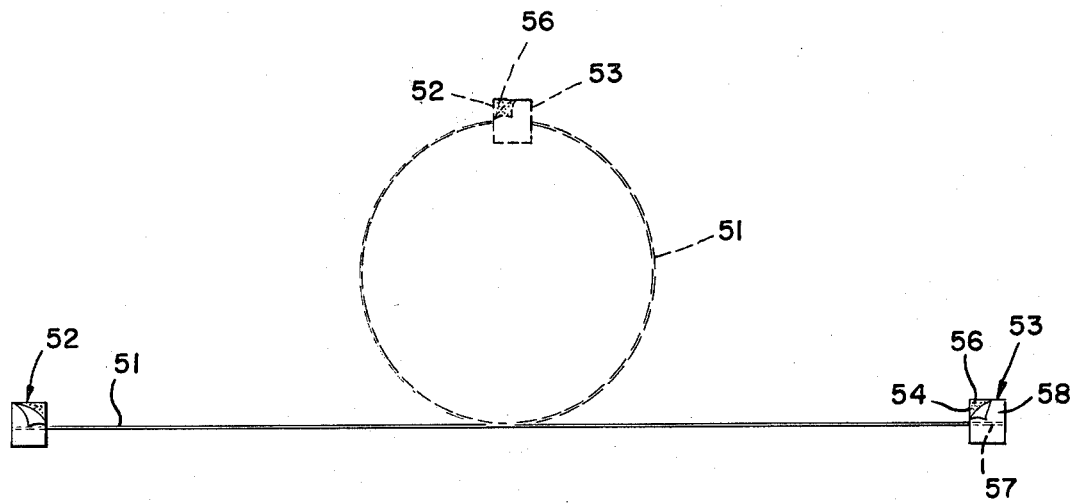
FIG. 11

DEVICE FOR CLEANING TEETH TO PREVENT THE FORMATION OF PLAQUE

BACKGROUND OF THE INVENTION

1. Field of the Invention

This invention relates to devices for "flossing" teeth, and particularly to a device including a thread-like member adapted to be tensioned by digital manipulation and to be drawn between adjacent teeth to abrade or scrape the tooth surfaces to dislodge and remove material adherent to the teeth that will develop into plaque if not removed.

2. Description of the Prior Art

The prior art relating to the subject matter of this invention is believed found in Class 132, sub-classes 84, 92, and 93; and Class 289, sub-classes 1.2, 1.5 and 18. A search of these classes and sub-classes has revealed the existence of U.S. Pat. Nos. 3,929,144 and 4,011,658. U.S. Pat. No. 3,929,144 relates to a floss threading device to enable the drawing of a length of dental floss through the interproximal area between two teeth whereupon the ends of the floss may be wrapped around the fingers in the conventional manner and the floss utilized in the conventional way. The reason for the need for such a device to literally draw the floss through the interproximal area is that the dentures are joined together, thus preventing the insertion of the floss between adjacent teeth. U.S. Pat. No. 4,011,658 relates to the method of threading a long filament through an interstice between the teeth as distinguished from the device utilized to effect such threading.

In modern times the term "floss" has come to mean, in relation to the cleansing of teeth, a thread-like material of indeterminate length and of sufficiently small transverse dimension to be forced between adjacent teeth and, after wrapping the ends of a length of the thread-like strand around the fingers, manipulated against the mutually facing surfaces of two adjacent teeth so as to dislodge and remove the soft sponge-like substance that collects on these surfaces and, which if not removed in some manner, becomes a hard plate-like crust known as "plaque".

Thus, the thread-like material for effecting this cleansing procedure has come to be known in its noun form as "floss", while the cleansing procedure has come to be known as a "flossing" procedure or action. The invention forming the subject matter of this invention relates to a device for effecting the cleansing procedure commonly known as "flossing" of the teeth through use of a floss-like or thread-like material. It is not intended however that the term "floss" be understood to describe, or be limited to, any specific material either in terms of its chemical or mechanical composition.

Thus, as used herein, the term "floss" is intended to cover any type of elongated flexible and/or limp material which is held taut by digitally imposed tension suitable for insertion between two adjacent teeth through the space that exists therebetween, or if the teeth abut one another, a material which may be squeezed between the abutting teeth so as to enter the interproximal area between the lower portion of the teeth next to the gum to permit manipulation of the material in such space in an abrading or scraping action against the opposed surfaces of the teeth individually or simultaniously.

Additionally, when used herein, the term "flossing" refers to the operation by which a length of material is inserted between two adjacent teeth and manipulated in such a way as to abrade the mutually facing surfaces of the teeth above the gum line so as to dislodge and remove soft substances adherent to such tooth surfaces.

It is generally recognized by the dental profession that daily "flossing" of the teeth is beneficial. It is also recognized by the dental profession, and has been demonstrated by users of conventional thread-like floss material that, at best, it is inconvenient, uncomfortable, unsanitary and distasteful to perform the "flossing" predure with conventional "floss" material in the form of an elongated strand. Accordingly, one of the objects of the present invention is to provide a device for "flossing" teeth that eliminate much of the inconvenience and discomfort, improves on the effectiveness, and to a large extent minimizes the distasteful aspects of the "flossing" procedure.

The vast majority of users of "floss" or thread-like or tape-like material for "flossing" the teeth cut approximately eighteen inches from a supply spool and proceed to rap the ends of this length of thread-like material about selected fingers of both hands to be able to impose tension on a short length of the thread-like material to thereby squeeze it between the teeth and manipulate it in a manner to perform the "flossing" procedure. It has been found that the greater portion of the strand is wrapped about the fingers and only a short length, approximately one inch, is inserted into the mouth between extended fingers, or finger and thumb. For performing the "flossing" procedure on the lower teeth, it is common practice to use the index fingers of both hands to manipulate the thread-like portion that is squeezed between the teeth. For performing the procedure on the upper teeth, most users utilize one or both thumbs in some manner to tension a short length of the thread-like material and cause it to penetrate between the teeth where it is manipulated. Whether one is using the index fingers of both hands or the thumbs of both hands, this operation is tedious, uncomfortable, at times painful in that the thread-like material is thin enough to perform a cutting operation on the gums if it is not adequately controlled and brought in contact therewith and sawed back and forth.

Additionally, because so much of the length of thread-like material is wrapped about the fingers, it can cut off circulation to the fingers and thereby create an unpleasant and even painful sensation therein. Accordingly, another object of the invention is the provision of a device for cleansing the teeth that eliminates the necessity of girdling the fingers of both hands with the free ends of a length of thread-like material to effect a "flossing" procedure, and which can even be manipulated by one hand to perform the "flossing" procedure.

Thus, while the benefits of regular "flossing" of the teeth is widely acknowledged by the dental profession, the use of dental floss remains relatively limited to a small proportion of the population. It is believed that one of the reasons for this is the inconvenience and discomfort associated with the "flossing" procedure by those that are capable of performing the procedure, and the inability of others to perform the procedure because of the inability to manipulate the fingers once they have been girdled by a length of the thread-like material. Accordingly, still another object of the present invention is the provision of a device for "flossing" the teeth that need not be girdled about the fingers and which does not require the use of any kind of a holding device for the thread-like material, and which does not require the insertion into the oral cavity of anything but two of the fingers of the person performing the procedure, and which can even be performed by persons handicapped with minimum digital dexterity, such as arthritics and other invalids.

One of the disadvantages of devices for holding a length of thread-like material for performing the "flossing" procedure is that these devices do not provide or enable control in that they rarely hold the thread-like material with sufficient tension while permitting manipulation of the tensioned thread-like length between adjacent teeth. On the otherhand if the tension is excessive, the thread-like strand will not conform to tooth surfaces and will therefore not clean these surfaces. Accordingly, still another object of the invention is the provision of the device for "flossing" the teeth that allows the user to easily and effectively control the tension of the floss material that extends between the teeth and which is easily and conveniently manipulable so as to apply the appropriate abrading force on the tooth surfaces.

In the conventional method of "flossing" teeth with a length of floss material wrapped about the fingers, whenever an unused portion of the floss material is to be used, a length thereof must be unwrapped from one finger on one hand and another portion wrapped onto a finger of the other hand. This is an inconvenient and sometimes difficult procedure to effect for the reason that the wet thread-like material becomes slippery and is difficult to grasp so as to impose the appropriate tension thereon. This is the basic reason why the free ends of the material must be wrapped or girdled about the fingers. Accordingly, a still further object of the present invention is the provision of a device for "flossing" the teeth which permits utilization of the entire length of a thread-like floss material without the necessity of wrapping the material about the fingers and without the inconvenience of the material slipping from the fingers because it is wet and slippery.

Persons with poor or no vision have difficulty manipulating floss to obtain proper tension. Persons with arthritis or other infirmities of the fingers also have difficulty manipulating floss, especially individuals who have use of only one hand. Accordingly, still another object is the provision of a device that may easily and comfortably be utilized by these types of individuals.

An important consideration in the use of any device for "flossing" the teeth is the safety with which the device may be used. The tissue within the oral cavity is delicate and easily injured. The tendency of "flossing" the teeth in the usual or conventional manner utilizing an inordinate length of thread-like material wrapped about the fingers of both hands and which becomes slippery with use and therefore hard to hold, especially under tension, frequently results in the fingers slipping from the thread-like material and obviously presents the danger of gouging the interior surfaces of the oral cavity with the fingernails. Accordingly, a still further object of the present invention is the provision of a device for "flossing" the teeth that precludes or minimizes this danger.

It has been found that the objects set forth above may be most easily achieved by formation of a length of thread-like material suitable for "flossing" teeth into a closed loop so that tension may be applied on any selected portion of the loop that is inserted between the teeth to effect the "flossing" procedure. Accordingly it is a still further object of the invention to provide a device comprising a closed loop formed to include a length of thread-like material effective for "flossing" the teeth.

A further object of the invention is to provide a device comprising a closed loop of floss the entire length of which may be used until worn out, so that less floss material will be consumed, thereby promoting a general saving of fuel energy through reduction of the amount of floss material that need be produced.

The invention possesses other objects and features of advantage, some of which, with the foregoing, will be apparent from the following description and the drawings. It is to be understood however that the invention is not limited to the embodiment illustrated and described, since it may be embodied in various forms within the scope of the appended claims.

SUMMARY OF THE INVENTION

In terms of broad inclusion, the device forming the subject matter of this invention in one aspect comprises a flexible closed loop at least a portion of which is formed from a flexible and limp thread-like material suitable for "flossing" the teeth, with the remainder of the closed loop being formed either from the same material or a different material capable of being manipulated as a closed loop.

In another aspect, the invention comprises a length of thread-like material suitable for "flossing" the teeth and which is provided on opposite ends with suitable means for joining those ends to form a closed and flexible limp loop.

In still another aspect, the invention comprises a pair of strands of material at least one of which is suitable for "flossing" the teeth, the associated ends of which may be joined by any suitable means to form a flexible limp loop through which the fingers of one or both hands may extend so as to impose tension on the loop without disengaging the engaged ends of the strands.

A fourth aspect of the invention includes the concept of the formation of a series of interconnected loops of material suitable for "flossing" the teeth, with individual loops being separately detachable from the chain or series thereof for appropriate use in "flossing" the teeth.

BRIEF DESCRIPTION OF THE DRAWINGS

FIG. 11 is another embodiment illustrating a strand of thread-like flexible material provided with adhesive coated tabs at opposite ends that may be overlapped as indicated in broken lines to form a closed loop.

FIG. 12 is another embodiment illustrating a strand of thread-like flexible material provided at opposite ends with a hook and "eye" adapted to be interengaged to form a closed limp loop.

FIG. 13 is still another embodiment illustrating a strand of flexible thread-like "flossing" material the opposite ends of which are gathered together and clamped between a suitable clamp means to retain the remainder of the strand in the form of a limp and flexible closed loop.

FIG. 14 is another embodiment in which a strand of the "flossing" material forms only a portion of a limp and flexible closed loop.

FIG. 15 is a perspective view illustrating how the limp and flexible closed loop "flossing" device of the invention is grasped by the fingers to impose tension on a short length thereof intended to be inserted between the teeth.

DESCRIPTION OF THE PREFERRED EMBODIMENT

Figure 1:
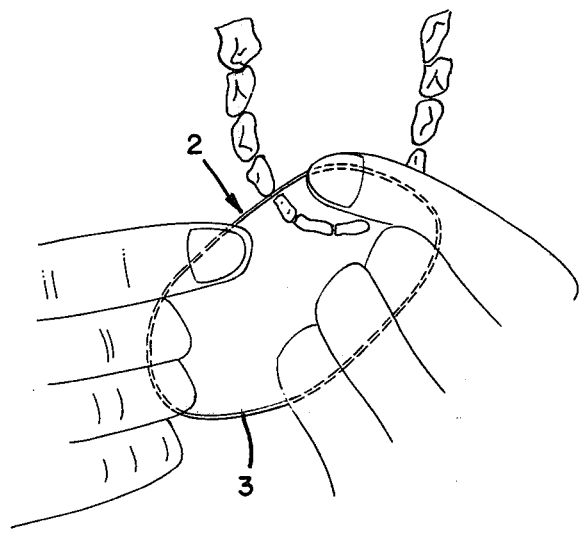
FIG. 1 is a perspective view illustrating the manner of use of the "flossing" device of the invention.
Figure 2:
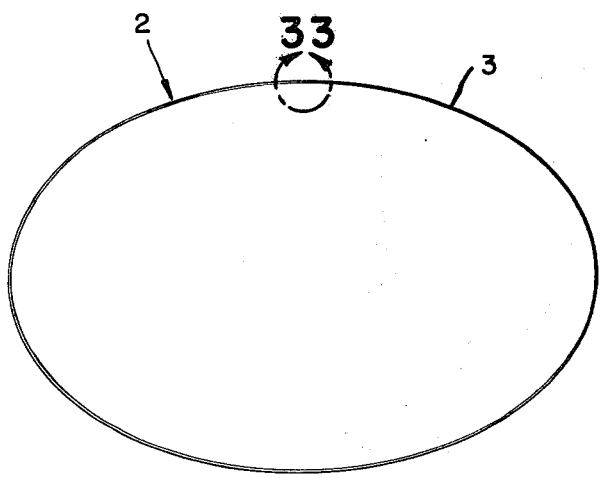
FIG. 2 is a perspective view of the device in one of its aspects.
Figure 3:
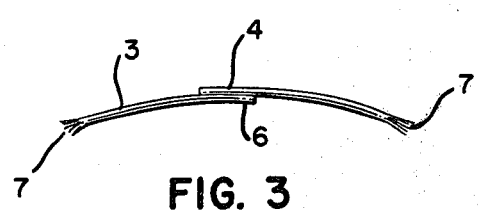
FIG. 3 is an enlarged fragmentary elevation illustrating the interconnection of the overlapped ends of the strand of flexible material illustrated in FIG. 2 for the purpose of forming a closed limp loop.

In terms of greater detail, the device for cleaning teeth to prevent the formation of plaque thereon comprises in a broad aspect as depicted in FIGS. 1 and 2, a flexible and limp closed loop designated generally by the numeral 2 and including a strand 3 of suitable length formed from a suitable material for "flossing" teeth. With respect to length, the strand 3 as depicted in FIGS. 1 and 2, is preferably approximately 6 to 12 inches long and formed into a closed loop by having the opposite end portions 4 and 6, as depicted in FIG. 3, overlapped as shown and suitably secured as by the use of an adhesive appropriate to the type of material used, or alternatively, the overlapped end portions 4 and 6 of the strand may be electronically "welded" so as to make a permanent and strong union having sufficient strength to withstand whatever tension is required to be imposed on it during the "flossing" procedure.

In terms of material, the strand 3 may be formed from any material that is suitable for drawing between the teeth to apply an abrading or scraping action on the mutually facing surfaces of adjacent teeth for the purpose of removing soft, aherent substances therefrom which if not removed, is converted into plaque by the chemical action continuously working in the mouth. It should be understood that in most instances the abrading or scraping action is not effected by drawing the strand longitudinally along its own axis. Rather, the abrading or scraping action occurs when the strand material is moved transversely of its own longitudinal axis while being pressed against a tooth so as to produce a scraping action on the surface of the tooth.

In this respect, since the opposing surfaces of adjacent teeth in most instances are curved, to be most effective, the strand must be flexible so that by appropriate digital manipulation the strand may be pressed against the surface to be abraded so as to conform the strand to the surface so that transverse movement of the strand along the surface effects the scraping action over even the curved surfaces of the tooth. It has been found that the strand 3 may be formed from a single filament having an appropriate thickness to be squeezed between closely adjacent teeth. Preferably, however, the strand 3 is formed of a multiplicity of separate filaments so that the total girth of the strand made up by the multiplicity of filaments is only a few thousandths of an inch thick. The advantage of forming the strand from a multiplicity of separate filaments is that tension imposed on the strand when pressed against a tooth surface causes the strand to flatten out so that the effective girth of the strand in one plane, for instance the plane of the crevice through which it must be squeezed to reach its ultimate position between the teeth, becomes no more than the thickness of the individual strands, thus enabling passage of the whole strand through crevices which are effectively of less width than the unstressed girth of the strand 3. This construction is illustrated in FIG. 3 where the separate filaments 7 are shown to form the composite strand 3. It should be noted also that for the strand composed of a multiplicity of separate filaments to function in the manner described above, i.e., flattening to reduce the girth, it is preferable that the strand filaments not be twisted in the manner in which a rope is twisted for the reason that the flattening effect would be more difficult to achieve. However, in instances where it is not necessary or desirable that the flattening effect be produced, it is obvious that the strand 3 may be formed from a multiplicity of twisted or braided filaments to form a string or rope-like strand of constant diameter.

Figure 4:
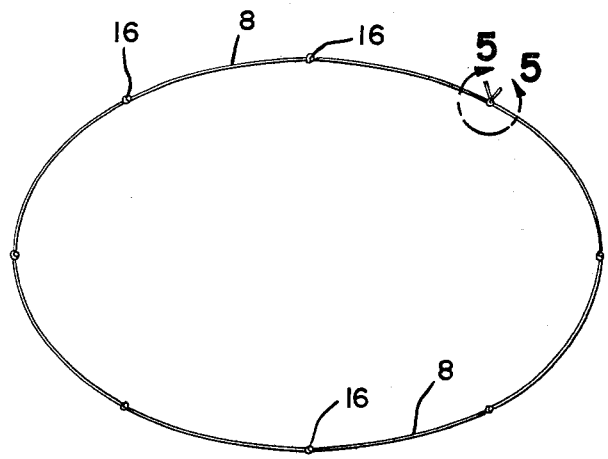
FIG. 4 illustrates a second embodiment of the closed loop "flossing" device.
Figure 5:
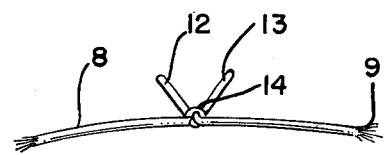
FIG. 5 is a fragmentary enlarged elevation illustrating the manner of interconnection of the opposite ends of the strand of thread-like material to form a closed limp loop.
Figure 8:
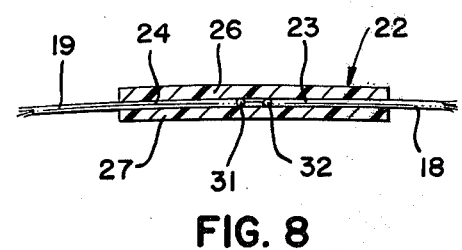
FIG. 8 is a vertical cross-sectional view taken in the plane indicated by the line 8—8 in FIG. 6.

Referring to FIGS. 4 and 5, there is there shown another method of joining the opposite ends of a strand 8. In this embodiment, the strand 8 is again formed of a multiplicity of separate filaments 9 and the opposite ends 12 and 13 are tied to form a knot 14 as shown best in FIG. 5. Additionally, along the length of the strand 8 there are formed individual knots 16 at spaced intervals as shown, each of the knots 16 forming a nodule which at that location in the strand increases its girth or thickness. As discussed above, when a strand of "flossing" material is used in the teeth cleansing procedure, it becomes wet and slippery. It thus becomes difficult to hold the strand and prevent its movement relative to the fingers. It has been found that by providing knots 16 spaced around the length of the strand, there is provided a slight thickness or abutment that may be utilized by the fingers to anchor the strand to the fingers and thereby prevent inadvertent displacement or relative movement between the strand and the fingers.

Additionally, while the primary movement of the strand to effect cleansing of tooth surfaces is a transverse movement, there are some instances in which the strand must be moved longitudinally along its own axis to effect a cleansing action. In these instances, the knot 16 functions as an abutment or scraping device as it moves along, dislodging and removing food particles from corners and crevices which might not otherwise be cleansed by a smooth strand as depicted in FIGS. 1 and 2. It should be understood however that the material from which the strand 8 is formed as depicted in FIGS. 4 and 5 may be the same material from which the flexible looped strand 3 is formed as depicted in FIGS. 1 and 2.

Figure 7:
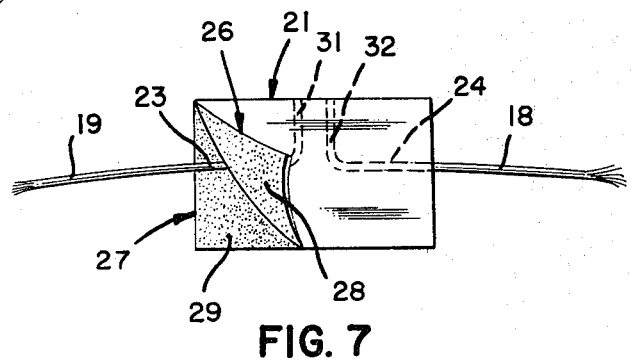
FIG. 7 is an enlarged fragmentary elevational view illustrating the manner of attachment of separate flexible strands of material to form a closed limp loop.
Figure 6:
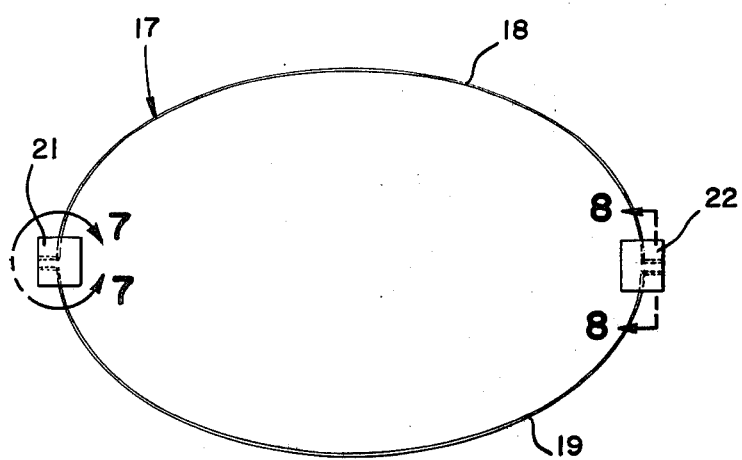
FIG. 6 is a plan view of a third embodiment of the "flossing" device.

Referring to FIGS. 6 and 7, the closed loop device is here designated by the numeral 17 and comprises a first strand 18 and a second strand 19, the opposite ends of which are firmly interengaged by appropriate double-thickness tabs 21 and 22 as illustrated. Strands 18 and 19 may be of different material and different thickness. As shown in larger scale in FIG. 7, the end portion 23 of strand 19 and the end portion 24 of strand 18 are generally axially aligned and sandwiched between the top layer 26 and the bottom layer 27 of the double-thickness tab 21, the opposed surfaces 28 and 29, of the tab members 26 and 27 respectively, being provided with an appropriate adhesive as shown, so that when the adhesive surfaces are pressed together, the strand portions 23 and 24 lie firmly caught between the adhesively retained layers 26 and 27.

While in most instances this is all that is required to retain the ends of the strands 18 and 19 from pulling apart, it has been found that added strength can be provided to the union by displacing end portions 31 and 32 of the strands 19 and 18, respectively, at right angles to the main body of the strand as illustrated in FIG. 7. Thus, tension imposed on the strands 18 and 19 must not only overcome the resistance imposed by the adhesive layers 26 and 27 on end portions 23 and 24, but must also overcome the added resistance provided by the right angle portions 31 and 32.

While the tabs 21 and 22 have been indicated as substantially larger than the strands 18 and 19, it will be apparent that the size of these tabs may be increased or decreased, depending upon what is convenient for the user. In any event, the strands 18 and 19 may be formed from the same material discussed above in connection with the embodiment illustrated in FIGS. 1–2 and FIGS. 4–5, and joined together as illustrated in FIG. 6, may be proportioned to provide a loop having a diameter of approximately two to four inches so that the loop may be conveniently manipulated as illustrated in FIG. 1. It will of course be obvious that the strands 18 and 19 may be fabricated from different materials to provide two different degrees of abrasiveness or scraping action.

Figure 9:
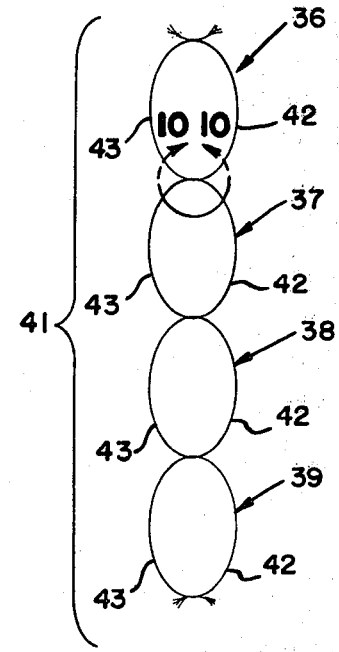
FIG. 9 illustrates the closed limp loop "flossing" device of the invention interconnected with like devices in a continuous series thereof to form a chain.
Figure 10:
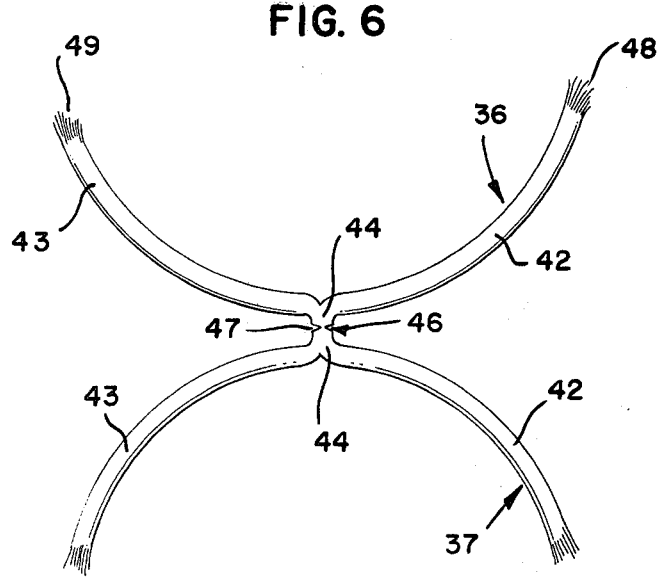
FIG. 10 is an enlarged fragmentary elevational view illustrating one means of interconnecting the loops of FIG. 9.

The embodiment of the invention as illustrated in FIGS. 9 and 10 is a departure in that a multiplicity of loops designated generally by the numerals 36, 37, 38 and 39 are joined together to form an elongated series or chain 41 of interconnected loops, the chain being formed in an indeterminate length. Each of the loops may be fabricated from the same material as discussed above in connection with the embodiment illustrated in FIGS. 1 and 2, or of two different materials having different characteristics, and each loop comprises an elongated strand 42 joined to a complimentary strand 43 at a jointure 44 which may be formed as previously described by appropriate electronic "welding" or bonding of the strands together to form a cohesive mass in the area designated 44 which immediately after jointure, connects two adjacent loops as illustrated by a thin neck portion 46 constituting a frangible or easily broken interconnection between adjacent loops so that one loop may be separated from the remainder of the chain merely by a sharp tug.

As illustrated in FIG. 10, the frangible or breakable neck 46 may be formed by providing transversely extending notches 47 in the cohesive mass of strands at their jointure. As before, the strands 42 and 43 are preferably formed from a multiplicity of separate filaments 48 and 49 gathered together to form single strands. When it is desired to use one of the loops in the chain 41, all that is required is that a sharp tug be given to the end loop, whereupon it is detached from the remainder of the chain and may then be used in the manner previously described. The closed loops are preferably approximately two to four inches in diameter so as to permit manipulation of any portion of the closed loop in the manner indicated in FIG. 1.

As previously stated, it is believed that the invention herein constitutes a flexible and limp closed loop at least a portion of which constitutes a strand of "flossing" material, with the closed loop being flexible and of such diameter that selected fingers of the person using the device may be inserted through the device so as to impose tension on selected portions thereof. It is the intention of the inventor herein to cover any form of connection of the ends of a strand of "flossing" material, or any type of material suitable for "flossing" the teeth, and with such intention in mind, reference is made to FIG. 11, in which a strand 51 of "flossing" material is provided at opposite ends with tabs 52 and 53, each of the tabs, as illustrated at the right of FIG. 11, being formed by a rectangular piece 54 of plastic or other suitable material, one surface of which is provided with a layer of adhesive 56. The end portion 57 of the strand 51 extends across the surface coated with adhesive 56 and in intimate contact therewith whereby the end portion 57 is adhesively adherred to the tab 53.

At the time of manufacture, the adhesive surface 56 of the rectangular or square piece 54 is covered by a protective sheet 58 that may be stripped off at time of use as partially illustrated at the left and right hand side of FIG. 11, so that the adhesive surfaces 56 of the tabs at opposite ends of the strand 51 may be brought together and overlapped in the manner illustrated in broken lines in FIG. 11. The opposite ends of the strand 51 of predetermined length are thus securely permanently joined, sandwiching the ends of the strand together in the adhesive layer, thus preventing their being disengaged, and permitting the fingers of one or both hands to be inserted in the loop thus formed, as illustrated in FIGS. 1 and 15. The device may now be used in the manner previously explained for the purpose of abrading selected surfaces of the teeth.

The embodiment of the invention illustrated in FIG. 12 discloses another means of joining the opposite ends of a strand of "flossing" material to form a closed loop. As there shown, the strand 61 is provided at one end with a hook member 62 adapted to engage an eye member 63 attached to the opposite end of the strand 61. As before, the strand is preferably formed from a multiplicity of individual filaments gathered to form the strand, and is preferably formed from conventional "flossing" material, although other forms of materials are not excluded.

In the interest of brevity, the specific method of attachment of the hook member 62 to the end of the strand 61 is not described inasmuch as any conventional method for securing two such members may be utilized. For the same reason, eye 63 is shown attached to the opposite end of the strand 61, but in the interest of brevity the method of attachment has not been described in detail. It will be seen that when the hook member 62 is engaged in the eye 63, a complete closed loop is formed through which the fingers of the user may be inserted as illustrated in FIGS. 1 and 15, placing tension on the jointure 62–63 to prevent its detachment during use. The loop of "flossing" material is then used in the usual manner as described above in connection with the embodiment illustrated in FIGS. 1 and 2.

It is important to emphasize that the invention in a broad aspect comprises a device that is a flexible and limp closed loop or a device that may be formed into such a closed loop of sufficient diameter that the fingers of one or both hands may be engaged in the loop in the manner illustrated in FIGS. 1 and 15, or in such other manner as may be convenient to the user. Thus, to accomplish formation of a closed loop from a strand of "flossing" material, it is the intention that any suitable means may be utilized for that purpose. In this vein, reference being had to FIG. 13, it will be seen that as there shown the strand 64 of "flossing" material, which may be similar to the material discussed above in connection with the other embodiments, is simply doubled back upon itself to provide a loop 66 having a diameter of approximately two to four inches, with the end portions 67 and 68 clamped together by an appropriate clamping member 69 as shown. The clamping member 69 need be no more than two plates held together by a rivet 71 so that the overlapping portions 72 and 73 bind the end portions of the strand tightly to prevent their inadvertent disengagement, but permit intentional removal. The closed loop of "flossing" material may now be used in a manner similar to the loops previously described.

The device illustrated in FIG. 14 also discloses a complete flexible closed loop designated generally by the numeral 76, and includes a strand 77 of a "flossing" material having opposite ends 78 and 79 thereof appropriately permanently secured to the associated ends of an intermediate loop-forming flexible strip or strand 81 which may or may not be a strand of "flossing" material. The strand 77 is preferably formed from the same type of material utilized to form the loop devices illustrated in FIGS. 1-13, and the end portions 78-79 are attached to the associated ends of the flexible strip or strand 81 so that the entire loop 76 thereby formed is flexible and of sufficient diameter, in the order of approximately two to four inches, or larger or smaller if convenient, to be digitally manipulated by inserting fingers through the loop.

One of the advantages of the device described above for cleansing teeth is that the closed flexible loop facilitates grasping of the very thin strand to prevent or minimize slipping through the fingers when digitally manipulated as shown in FIG. 1, where it is seen that the index fingers of both hands are utilized to manipulate a short length of the strand, considerably shorter than its entire length, between two teeth to be abraded to effect an abrading action against the opposed surfaces thereof. Note that in FIG. 1 the fingers of both hands may be in the relative positions indicated, with the index fingers being placed above the strand closely adjacent the teeth, and the remaining fingers extending through the loop to thereby impose tension therein over the pads on the finger tips on the index fingers. This appears to be a convenient arrangement of the fingers in relation to the closed-loop cleansing device for application to the lower set of teeth. A further illustration of this is provided in FIG. 15, where it is seen that the strand formed into a closed loop designated by the numeral 2 crosses over the pads on the ends of the index fingers and the loop is grasped by the next two succeeding fingers passing through the loop, with the little fingers of both hands remaining outside the loop. Obviously, when convenient, all four fingers of both hands may be inserted through the loop, or fewer fingers than those shown, including only selected fingers of one hand, may be used, depending on the convenience of the user.

It has been found that when the closed loop device for cleansing teeth is utilized to clean the upper teeth in the mouth, it is most convenient that the fingers of both hands be interengaged with the closed loop in such a manner that the index finger of one hand and the thumb of the other hand be utilized to digitally manipulate a short section of the closed loop device into the mouth and into abrading engagement between the teeth. In some instances, the thumb over which the closed loop section is held will be outside the mouth, while the index finger over which the strand is held will be inserted inside the mouth.

Having thus described the invention, what is claimed to be new and novel and sought to be protected by Letters Patent of the United States is as follows:

1. A device for cleaning teeth, comprising:
   a first flexible strand of predetermined length having first and second ends;
   a second flexible strand of predetermined length having first and second ends, said first and second strands forming a pair of strands, corresponding first and second ends of said pair of strands being in close proximity, said strands being of sufficient length to form, when said corresponding first and second ends are joined, a single closed loop large enough for at least one finger of each hand of the user to penetrate the loop; and
   first and second adhesive tab means joining corresponding first ends and corresponding second ends, respectively, of said pair of strands to complete a single, closed, flexible and limp loop.

2. The combination according to claim 1, in which said first and second adhesive tab means each comprises a pair of adhesive layers between which two corresponding ends are sandwiched.

3. The combination according to claim 2, in which said corresponding first and said corresponding second ends in close proximity are axially aligned.

4. The combination according to claim 2, in which a portion of each of said corresponding first and second ends sandwiched between respective adhesive layers is perpendicular to the remainder of its corresponding end.

5. As an article of manufacture:
   (a) first and second strands of dental "floss" material of predetermined length having corresponding end portions in close proximity, said strands being of sufficient length to form, when joined end to end, a loop large enough to admit at least two fingers of the user; and
   (b) a pair of doubled-thickness tab means interengageable with corresponding end portions of said strands of dental "floss" material to form a closed loop of said strand, each of said tab means comprising a top layer and a bottom layer having opposed surfaces, and adhesive means on at least one of said opposed surfaces to secure said layers together, the corresponding end portions of said strands being sandwiched between said layers.

6. The article of claim 5, wherein said strands are of different thicknesses.

7. The article of claim 5, wherein corresponding end portions of said strands are secured in axial alignment by said tab means.

8. The article of claim 7, wherein the ends of said strands are displaced at right angles to said end portions within said tab means.

9. A device for cleaning teeth, comprising:
   (a) a strand of dental floss material of predetermined length and having first and second ends, said strand being of sufficient length to form a single loop large enough to admit at least two fingers of a user; and (b) joining means comprising a first tab means engaging said first end and second tab means engaging said second end of said strand to complete a single closed loop, each of said first and second tab means having adhesive on one side thereof and being secured to its corresponding strand end and each tab having protective film removably superimposed on said adhesive whereby said tab means on opposite end portions of the strand may be adhesively joined when the protective film is removed from each tab means, said tab means being sufficiently small to permit use of the entire length of said strand loop for cleaning teeth.

* * * * *